United States Patent
Doyle et al.

(10) Patent No.: US 12,220,575 B2
(45) Date of Patent: Feb. 11, 2025

(54) INTRAVENOUS / INTRA-SPINAL / INTRA-CAVITY / INTRAVENTRICULAR DELIVERY OF TTFIELDS (TUMOR TREATING FIELDS) FOR TREATING CANCER AND METASTASES

(71) Applicant: Novocure GmbH, Root (CH)

(72) Inventors: William Doyle, Malvern, PA (US); Richard Deslauriers, Woodbury, CT (US)

(73) Assignee: Novocure GmbH, Root D4 (CH)

(*) Notice: Subject to any disclaimer, the term of this patent is extended or adjusted under 35 U.S.C. 154(b) by 0 days.

(21) Appl. No.: 18/383,575

(22) Filed: Oct. 25, 2023

(65) Prior Publication Data

US 2024/0058604 A1  Feb. 22, 2024

Related U.S. Application Data

(62) Division of application No. 17/213,985, filed on Mar. 26, 2021, now abandoned.

(60) Provisional application No. 63/002,042, filed on Mar. 30, 2020.

(51) Int. Cl.
*A61N 1/36* (2006.01)
*A61N 1/05* (2006.01)
*A61N 1/375* (2006.01)

(52) U.S. Cl.
CPC ....... *A61N 1/36002* (2017.08); *A61N 1/0551* (2013.01); *A61N 1/37516* (2017.08)

(58) Field of Classification Search
CPC .............. A61N 1/36002; A61N 1/0551; A61N 1/37516; A61N 1/36017; A61N 1/0529; A61N 1/05; A61N 1/40
See application file for complete search history.

(56) References Cited

U.S. PATENT DOCUMENTS

| 6,868,289 B2 | 3/2005 | Palti |
| 7,016,725 B2 | 3/2006 | Palti |
| 7,089,054 B2 | 8/2006 | Palti |

(Continued)

FOREIGN PATENT DOCUMENTS

WO  2020219517 A2  10/2020

OTHER PUBLICATIONS

International Search Report and Written Opinion issued in application No. PCT/IB2021/052538 dated Jul. 1, 2021.

*Primary Examiner* — Rex R Holmes
(74) *Attorney, Agent, or Firm* — Potomac Law Group, PLLC

(57) ABSTRACT

Tumor treating fields (TTFields) may be applied to a person's body using six different types of electrodes. More specifically, the electrodes may be shaped and dimensioned (a) for insertion into blood vessels so that they make contact with the person's blood; (b) for insertion into a central canal of a spinal cord, so that they make contact with the CSF; (c) for insertion into a body orifice at a position that contacts an interior surface of the person's body; (d) for affixation to skin of the person's body (e.g., on the person's head, torso, back, abdomen, etc.); (e) for insertion into a brain ventricle so that they make contact with the person's CSF; or (f) for insertion into lymph vessels so that they make contact with the person's lymph. Applying an AC voltage between any two of these electrodes will create TTFields in respective parts of the person's body.

6 Claims, 13 Drawing Sheets

(56) References Cited

U.S. PATENT DOCUMENTS

| | | |
|---|---|---|
| 7,136,699 B2 | 11/2006 | Palti |
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,145,316 B2 | 3/2012 | Deem et al. |
| 8,170,684 B2 | 5/2012 | Palti |
| 8,175,698 B2 | 5/2012 | Palti et al. |
| 8,229,555 B2 | 7/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 10,953,209 B2 | 3/2021 | Story et al. |
| 2002/0055764 A1 | 5/2002 | Malonek et al. |
| 2004/0010290 A1 | 1/2004 | Schroeppel et al. |
| 2004/0068296 A1 | 4/2004 | Palti |
| 2005/0085884 A1 | 4/2005 | O'Brien et al. |
| 2006/0064150 A1 | 3/2006 | Heist et al. |
| 2006/0167499 A1 | 7/2006 | Palti |
| 2006/0282122 A1 | 12/2006 | Palti |
| 2007/0033660 A1 | 2/2007 | Palti |
| 2007/0225766 A1 | 9/2007 | Palti |
| 2007/0239213 A1 | 10/2007 | Palti |
| 2008/0140000 A1 | 6/2008 | Shuros et al. |
| 2009/0076366 A1 | 3/2009 | Palti |
| 2010/0228310 A1* | 9/2010 | Shuros .............. A61N 1/36114 607/72 |
| 2011/0137229 A1 | 6/2011 | Palti et al. |
| 2012/0283726 A1 | 11/2012 | Palti |
| 2013/0165920 A1 | 6/2013 | Weber et al. |
| 2013/0178819 A1 | 7/2013 | Palti et al. |
| 2013/0178820 A1 | 7/2013 | Palti et al. |
| 2013/0184637 A1 | 7/2013 | Palti |
| 2013/0184674 A1 | 7/2013 | Palti |
| 2014/0296948 A1 | 10/2014 | Sluijter |
| 2014/0330268 A1 | 11/2014 | Palti et al. |
| 2015/0005680 A1 | 1/2015 | Lipani |
| 2015/0320478 A1 | 11/2015 | Cosman, Jr. et al. |
| 2017/0050041 A1 | 2/2017 | Cosman |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2018/0264260 A1 | 9/2018 | Zarins |
| 2019/0117956 A1 | 4/2019 | Wenger et al. |
| 2019/0117963 A1 | 4/2019 | Travers et al. |
| 2019/0117969 A1 | 4/2019 | Schmidt et al. |
| 2019/0117970 A1 | 4/2019 | Schmidt et al. |
| 2019/0117972 A1 | 4/2019 | Schmidt et al. |
| 2019/0117973 A1 | 4/2019 | Schmidt et al. |
| 2019/0160291 A1 | 5/2019 | Peichel et al. |
| 2019/0307781 A1 | 10/2019 | Krex et al. |
| 2019/0308016 A1 | 10/2019 | Wenger et al. |
| 2019/0314631 A1 | 10/2019 | Wong et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0016399 A1 | 1/2020 | Kaynan et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0114142 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |
| 2020/0368525 A1 | 11/2020 | Maag et al. |
| 2021/0000528 A1 | 1/2021 | Palti et al. |
| 2021/0008367 A1 | 1/2021 | Giladi et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |

\* cited by examiner

INTRAVENOUS / INTRA-SPINAL / INTRA-CAVITY / INTRAVENTRICULAR DELIVERY OF TTFIELDS (TUMOR TREATING FIELDS) FOR TREATING CANCER AND METASTASES

CROSS REFERENCE TO RELATED APPLICATIONS

This application is a divisional of U.S. application Ser. No. 17/213,985, filed Mar. 26, 2021, which claims the benefit of U.S. Provisional Application 63/002,042, filed Mar. 30, 2020, each of which is incorporated herein by reference in its entirety.

BACKGROUND

TTFields are low intensity (e.g., 1-4 V/cm) alternating electric fields within the intermediate frequency range (e.g., 100-300 kHz), which may be used, for example, to treat tumors as described in U.S. Pat. No. 7,565,205, which is incorporated herein by reference in its entirety. TTFields therapy is an approved mono-treatment for recurrent glioblastoma (GBM), and an approved combination therapy with chemotherapy for newly diagnosed GBM patients. TTFields can also be used to treat tumors in other parts of a person's body (e.g., lungs, ovaries, pancreas). TTFields are induced non-invasively into the target region by transducer arrays (i.e., arrays of capacitively coupled electrode elements) placed directly on the patient's skin (e.g., using the Novocure Optune® system).

The conventional layout for positioning transducer arrays on a person's body is to place one pair of transducer arrays on the person's skin in front/back of the afflicted body part, and another pair of transducer arrays on the person's skin to the right/left of the afflicted body part. For example, in the context of glioblastoma, one pair of transducer arrays is positioned on the person's skin on the front and back of the head, and another pair of transducer arrays is positioned on the person's skin on the right and left sides of the head. An AC voltage generator applies an AC voltage (e.g., 200 kHz) between the front and back transducer arrays for a first interval of time (e.g., one second), which generates an electric field with field lines that generally run in a front/back direction. Then, the AC voltage generator applies an AC voltage at the same frequency between the right and left transducer arrays for a second interval of time (e.g., one second), which generates an electric field with field lines that generally run in a right/left direction. The system then repeats this two-step sequence for the duration of the treatment.

SUMMARY OF THE INVENTION

One aspect of the invention is directed to a first apparatus for creating an electric field in a portion of a person's body. The first apparatus comprises a first electrode, a second electrode, and an AC voltage generator. The first electrode is shaped and dimensioned for insertion into a blood vessel of the person's body or a central canal of a spinal cord of the person's body, and the first electrode has a biocompatible outer surface. The second electrode is shaped and dimensioned for either (a) insertion into a blood vessel of the person's body, (b) insertion into the central canal of the spinal cord of the person's body, (c) insertion into a body orifice of the person at a position that contacts an interior surface of the person's body, (d) affixation to skin of the person's body, or (e) insertion into a lymph vessel of the person's body. And the AC voltage generator is arranged to impose an AC voltage between the first electrode and the second electrode.

In some embodiments of the first apparatus, the first electrode has a needle-shaped tip with a biocompatible outer surface. Optionally, in these embodiments, the needle-shaped tip has a blunt end.

In some embodiments of the first apparatus, the outer surface of the first electrode is conductive. In some embodiments of the first apparatus, the outer surface of the first electrode comprises pyrolytic carbon.

In some embodiments of the first apparatus, the first electrode has a conductive inner core and a dielectric layer disposed on the conductive inner core, and the outer surface of the first electrode is disposed on the dielectric layer and is conductive. Optionally, in these embodiments, the outer surface of the first electrode comprises pyrolytic carbon.

In some embodiments of the first apparatus, the first electrode is shaped and dimensioned for insertion into a first blood vessel of the person's body, and the second electrode is shaped and dimensioned for insertion into a second blood vessel of the person's body. In some embodiments of the first apparatus, the first electrode is shaped and dimensioned for insertion into the blood vessel of the person's body, and the second electrode is shaped and dimensioned for insertion into the central canal of the spinal cord of the person's body. In some embodiments of the first apparatus, the first electrode is shaped and dimensioned for insertion into the blood vessel of the person's body, and the second electrode is shaped and dimensioned for insertion into the body orifice of the person at a position that contacts the interior surface of the person's body. In some embodiments of the first apparatus, the first electrode is shaped and dimensioned for insertion into the blood vessel of the person's body, and the second electrode is shaped and dimensioned for affixation to skin of the person's body. In some embodiments of the first apparatus, the first electrode is shaped and dimensioned for insertion into the blood vessel of the person's body, and the second electrode is shaped and dimensioned for insertion into the lymph vessel of the person's body. In some embodiments of the first apparatus, the first electrode is shaped and dimensioned for insertion into the central canal of the spinal cord of the person's body, and the second electrode is shaped and dimensioned for insertion into the body orifice of the person at a position that contacts the interior surface of the person's body. In some embodiments of the first apparatus, the first electrode is shaped and dimensioned for insertion into the central canal of the spinal cord of the person's body, and the second electrode is shaped and dimensioned for affixation to skin of the person's body. In some embodiments of the first apparatus, the first electrode is shaped and dimensioned for insertion into the central canal of the spinal cord of the person's body, and the second electrode is shaped and dimensioned for insertion into the lymph vessel of the person's body.

In some embodiments of the first apparatus, the AC voltage generator generates an AC voltage having a frequency between 50 kHz and 500 kHz. In some embodiments of the first apparatus, the AC voltage generator generates an AC voltage having a frequency between 100 kHz and 300 kHz.

Some embodiments of the first apparatus further comprise a capacitor wired in series between the AC voltage generator and the first electrode. Some embodiments of the first apparatus further comprise a capacitor wired in series between the AC voltage generator and the second electrode.

Some embodiments of the first apparatus further comprise a plurality of third electrodes and a plurality of switches. Each of the third electrodes is shaped and dimensioned for either (a) insertion into a blood vessel of the person's body, (b) insertion into the central canal of the spinal cord of the person's body, (c) insertion into a body orifice of the person at a position that contacts an interior surface of the person's body, (d) affixation to skin of the person's body, or (e) insertion into a lymph vessel of the person's body. And the plurality of switches is arranged to selectively route the AC voltage between pairs of electrodes selected from the group consisting of the first electrode, the second electrode, and the plurality of third electrodes.

Another aspect of the invention is directed to a second apparatus for creating an electric field in a portion of a person's body. The second apparatus comprises a first electrode, a second electrode, and an AC voltage generator. The first electrode is shaped and dimensioned for insertion into a first body orifice of the person at a position that contacts a first interior surface of the person's body. The second electrode is shaped and dimensioned for either (a) insertion into a second body orifice of the person at a position that contacts a second interior surface of the person's body, or (b) affixation to skin of the person's body. And the AC voltage generator is arranged to impose an AC voltage between the first electrode and the second electrode.

In some embodiments of the second apparatus, the first electrode has a conductive outer surface. In some embodiments of the second apparatus, the first electrode has a conductive inner core, a dielectric layer disposed on the conductive inner core, and a conductive outer surface disposed on the dielectric layer. In some embodiments of the second apparatus, the second electrode is shaped and dimensioned for insertion into the second body orifice of the person at a position that contacts the second interior surface of the person's body. In some embodiments of the second apparatus, the second electrode is shaped and dimensioned for affixation to skin of the person's body. In some embodiments of the second apparatus, the first electrode is shaped and dimensioned to make contact with a hard palate of the person's mouth.

In some embodiments of the second apparatus, the AC voltage generator generates an AC voltage having a frequency between 50 kHz and 500 kHz. In some embodiments of the second apparatus, the AC voltage generator generates an AC voltage having a frequency between 100 kHz and 300 kHz.

Some embodiments of the second apparatus further comprise a capacitor wired in series between the AC voltage generator and the first electrode. Some embodiments of the second apparatus further comprise a capacitor wired in series between the AC voltage generator and the second electrode.

Some embodiments of the second apparatus further comprise a plurality of third electrodes and a plurality of switches. Each of the third electrodes is shaped and dimensioned for either (a) insertion into a body orifice of the person at a position that contacts an interior surface of the person's body, or (b) affixation to skin of the person's body. The plurality of switches is arranged to selectively route the AC voltage between pairs of electrodes selected from the group consisting of the first electrode, the second electrode, and the plurality of third electrodes.

Another aspect of the invention is directed to a first method of treating a portion of a person's body with an electric field. The first method comprises inserting a first electrode shaped into a blood vessel of the person's body or a central canal of a spinal cord of the person's body. The first electrode has a biocompatible outer surface. The first method also comprises positioning a second electrode on or in the person's body, wherein the second electrode is shaped and dimensioned for either (a) insertion into a blood vessel of the person's body, (b) insertion into the central canal of the spinal cord of the person's body, (c) insertion into a body orifice of the person at a position that contacts an interior surface of the person's body, (d) affixation to skin of the person's body, or (e) insertion into a lymph vessel of the person's body. And the first method also comprises applying an AC voltage between the first electrode and the second electrode.

In some instances of the first method, the outer surface of the first electrode is conductive. In some instances of the first method, the outer surface of the first electrode comprises pyrolytic carbon. In some instances of the first method, the first electrode has a conductive inner core and a dielectric layer disposed on the conductive inner core, and the outer surface of the first electrode is disposed on the dielectric layer and is conductive. Optionally, in these instances, the outer surface of the first electrode comprises pyrolytic carbon.

In some instances of the first method, the first electrode is inserted into a first blood vessel of the person's body that supplies oxygenated blood to a target organ, and the second electrode is inserted into a second blood vessel of the person's body that routes deoxygenated blood away from the target organ. In some instances of the first method, the first electrode is inserted into the blood vessel of the person's body, and the positioning of the second electrode comprises inserting the second electrode into the central canal of the spinal cord of the person's body. In some instances of the first method, the first electrode is inserted into the blood vessel of the person's body, and the positioning of the second electrode comprises inserting the second electrode into the body orifice of the person at a position that contacts the interior surface of the person's body. In some instances of the first method, the first electrode is inserted into the blood vessel of the person's body, and the positioning of the second electrode comprises affixing the second electrode to skin of the person's body. In some instances of the first method, the first electrode is inserted into the blood vessel of the person's body, and the positioning of the second electrode comprises inserting the second electrode into the lymph vessel of the person's body. In some instances of the first method, the first electrode is inserted into the central canal of the spinal cord of the person's body, and the positioning of the second electrode comprises inserting the second electrode into the body orifice of the person at a position that contacts the interior surface of the person's body. In some instances of the first method, the first electrode is inserted into the central canal of the spinal cord of the person's body, and the positioning of the second electrode comprises affixing the second electrode to skin of the person's body. In some instances of the first method, the first electrode is inserted into the central canal of the spinal cord of the person's body, and the positioning of the second electrode comprises inserting the second electrode into the lymph vessel of the person's body.

In some instances of the first method, the AC voltage has a frequency between 50 kHz and 500 kHz. In some instances of the first method, the AC voltage has a frequency between 100 kHz and 300 kHz.

Some instances of the first method further comprise positioning a capacitor in series with the first electrode.

Some instances of the first method further comprise positioning a capacitor in series with the second electrode.

Another aspect of the invention is directed to a second method of treating a portion of a person's body with an electric field. The second method comprises inserting a first electrode into a first body orifice of the person at a position that contacts a first interior surface of the person's body. The second method also comprises positioning a second electrode on or in the person's body, wherein the second electrode is shaped and dimensioned for either (a) insertion into a second body orifice of the person at a position that contacts a second interior surface of the person's body, or (b) affixation to skin of the person's body. The second method also comprises applying an AC voltage between the first electrode and the second electrode.

In some instances of the second method, the first electrode has a conductive outer surface. In some instances of the second method, the first electrode has a conductive inner core, a dielectric layer disposed on the conductive inner core, and a conductive outer surface disposed on the dielectric layer. In some instances of the second method, the positioning of the second electrode comprises inserting the second electrode into the second body orifice of the person at a position that contacts the second interior surface of the person's body. In some instances of the second method, the positioning of the second electrode comprises affixing the second electrode to skin of the person's body.

In some instances of the second method, the AC voltage has a frequency between 50 kHz and 500 kHz. In some instances of the second method, the AC voltage has a frequency between 100 kHz and 300 kHz.

Some instances of the second method further comprise positioning a capacitor in series with the first electrode. Some instances of the second method further comprise positioning a capacitor in series with the second electrode.

Another aspect of the invention is directed to a third apparatus for creating an electric field in a portion of a person's body. The third apparatus comprises a first electrode, a second electrode, and an AC voltage generator. The first electrode is shaped and dimensioned for insertion into a brain ventricle of the person's body. The first electrode has a biocompatible outer surface. The second electrode is shaped and dimensioned for either (a) insertion into a blood vessel of the person's body, (b) insertion into the central canal of the spinal cord of the person's body, (c) insertion into a body orifice of the person at a position that contacts an interior surface of the person's body, (d) affixation to skin of the person's body, or (e) insertion into a lymph vessel of the person's body. And the AC voltage generator is arranged to impose an AC voltage between the first electrode and the second electrode.

In some embodiments of the third apparatus, the outer surface of the first electrode is conductive. In some embodiments of the third apparatus, the outer surface of the first electrode comprises pyrolytic carbon.

In some embodiments of the third apparatus, the first electrode has a conductive inner core and a dielectric layer disposed on the conductive inner core, and the outer surface of the first electrode is disposed on the dielectric layer and is conductive. Optionally, in these embodiments, the outer surface of the first electrode comprises pyrolytic carbon.

In some embodiments of the third apparatus, the second electrode is shaped and dimensioned for insertion into the blood vessel of the person's body. In some embodiments of the third apparatus, the second electrode is shaped and dimensioned for insertion into the central canal of the spinal cord of the person's body. In some embodiments of the third apparatus, the second electrode is shaped and dimensioned for insertion into the body orifice of the person at a position that contacts the interior surface of the person's body. In some embodiments of the third apparatus, the second electrode is shaped and dimensioned for affixation to skin of the person's body. In some embodiments of the third apparatus, the second electrode is shaped and dimensioned for insertion into the lymph vessel of the person's body.

Some embodiments of the third apparatus further comprise a capacitor wired in series between the AC voltage generator and the first electrode. Some embodiments of the third apparatus further comprise a capacitor wired in series between the AC voltage generator and the second electrode.

Another aspect of the invention is directed to a third method of treating a portion of a person's body with an electric field. The third method comprises inserting a first electrode into a brain ventricle of the person's body. The first electrode has a biocompatible outer surface. The third method also comprises positioning a second electrode on or in the person's body, wherein the second electrode is shaped and dimensioned for either (a) insertion into a blood vessel of the person's body, (b) insertion into the central canal of the spinal cord of the person's body, (c) insertion into a body orifice of the person at a position that contacts an interior surface of the person's body, (d) affixation to skin of the person's body, or (e) insertion into a lymph vessel of the person's body. And the third method also comprises applying an AC voltage between the first electrode and the second electrode.

In some instances of the third method, the outer surface of the first electrode is conductive. In some instances of the third method, the outer surface of the first electrode comprises pyrolytic carbon.

In some instances of the third method, the first electrode has a conductive inner core and a dielectric layer disposed on the conductive inner core, and the outer surface of the first electrode is disposed on the dielectric layer and is conductive. Optionally, in these instances, the outer surface of the first electrode comprises pyrolytic carbon.

In some instances of the third method, the positioning of the second electrode comprises inserting the second electrode into a blood vessel of the person's body. In some instances of the third method, the positioning of the second electrode comprises inserting the second electrode into the central canal of the spinal cord of the person's body. In some instances of the third method, the positioning of the second electrode comprises inserting the second electrode into the body orifice of the person at a position that contacts the interior surface of the person's body. In some instances of the third method, the positioning of the second electrode comprises affixing the second electrode to skin of the person's body. In some instances of the third method, the positioning of the second electrode comprises inserting the second electrode into the lymph vessel of the person's body.

In some instances of the third method, the AC voltage has a frequency between 50 kHz and 500 kHz. In some instances of the third method, the AC voltage has a frequency between 100 kHz and 300 kHz.

Some instances of the third method further comprise positioning a capacitor in series with the first electrode. Some instances of the third method further comprise positioning a capacitor in series with the second electrode.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Although the conventional approach of positioning the transducer arrays on a person's skin works quite well in certain anatomic locations (e.g., for treating glioblastoma, pancreatic cancer, lung cancer, etc.), it may not be possible to create an electric field with a sufficient intensity or power density in all parts of a person's body that may require treatment using TTFields when the placement of the transducer arrays is confined to external surfaces of a person's body (i.e., skin).

The embodiments described herein provide new approaches for positioning the transducer arrays on or in a person's body. These embodiments can facilitate the creation of electric fields in parts of the body where it may not be possible to create a sufficiently strong electric field using transducer arrays that are only positioned on a person's skin.

Figure 1:
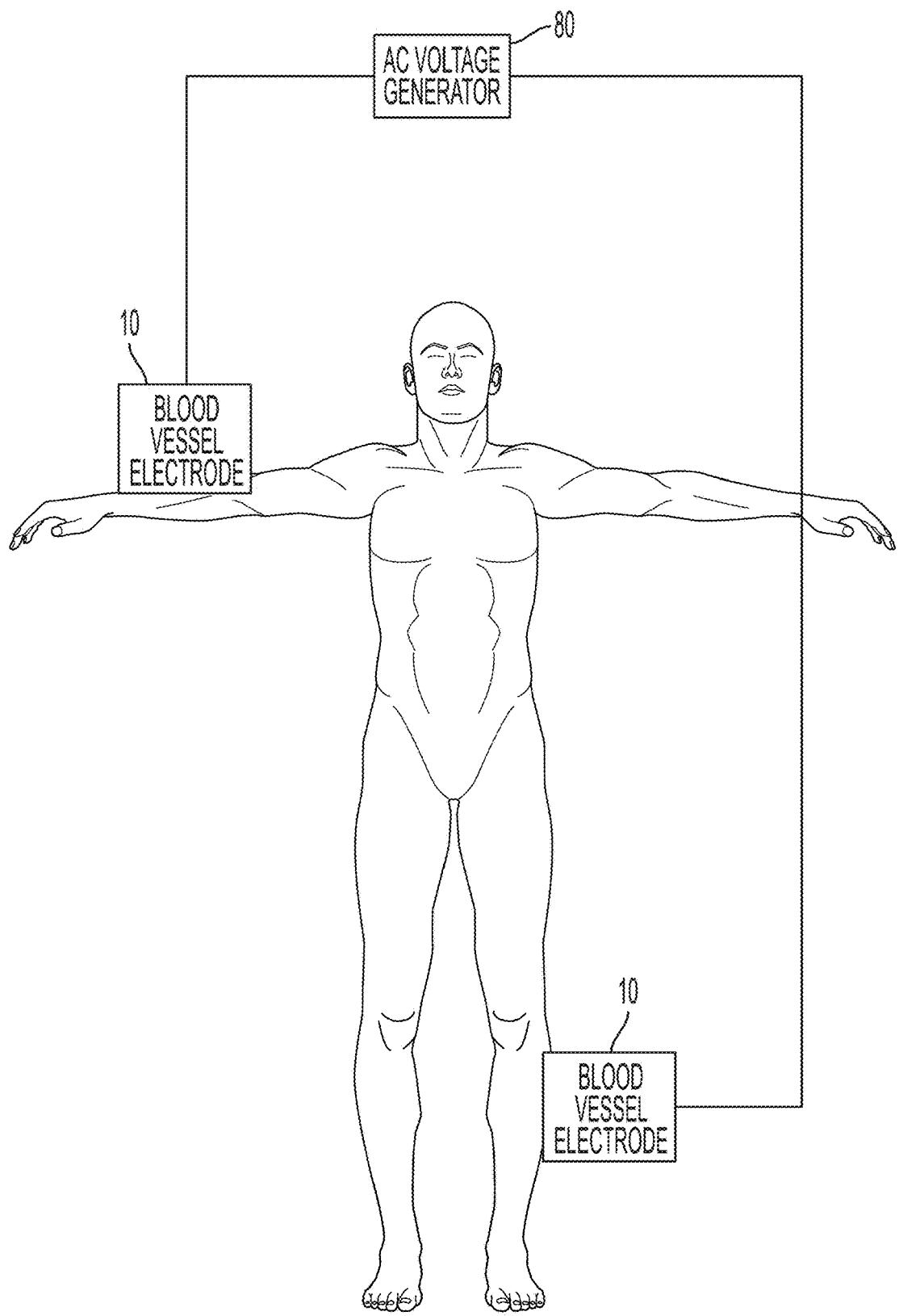
FIG. 1 is a schematic representation of a system for delivering TTFields using electrodes that are shaped and dimensioned for insertion into blood vessels.

FIG. 1 depicts a first alternative to the conventional external transducer arrays for applying TTFields to portions of a person's body. The first alternative uses two electrodes 10 that are shaped and dimensioned for insertion into blood vessels of the person's body so that they make contact with the person's blood. The outer surfaces of the electrodes 10 are biocompatible. In some embodiments, the electrodes 10 have needle-shaped tips, preferably with blunt ends. Examples of blood vessels into which the electrodes 10 can be inserted include, but are not limited to, the carotid artery, the jugular vein, radial arteries, shoulder arteries, femoral arteries, the superior vena cava, iliac veins, etc.

When two of these electrodes 10 are positioned in blood vessels in a person's body and connected to the AC voltage generator 80, the AC voltage generator will impose an AC voltage between the two electrodes 10. Because blood is a highly conductive substance, an electric field will be imposed in the person's body with field lines that run generally parallel to the person's blood vessels between the two electrodes 10.

Figure 9:
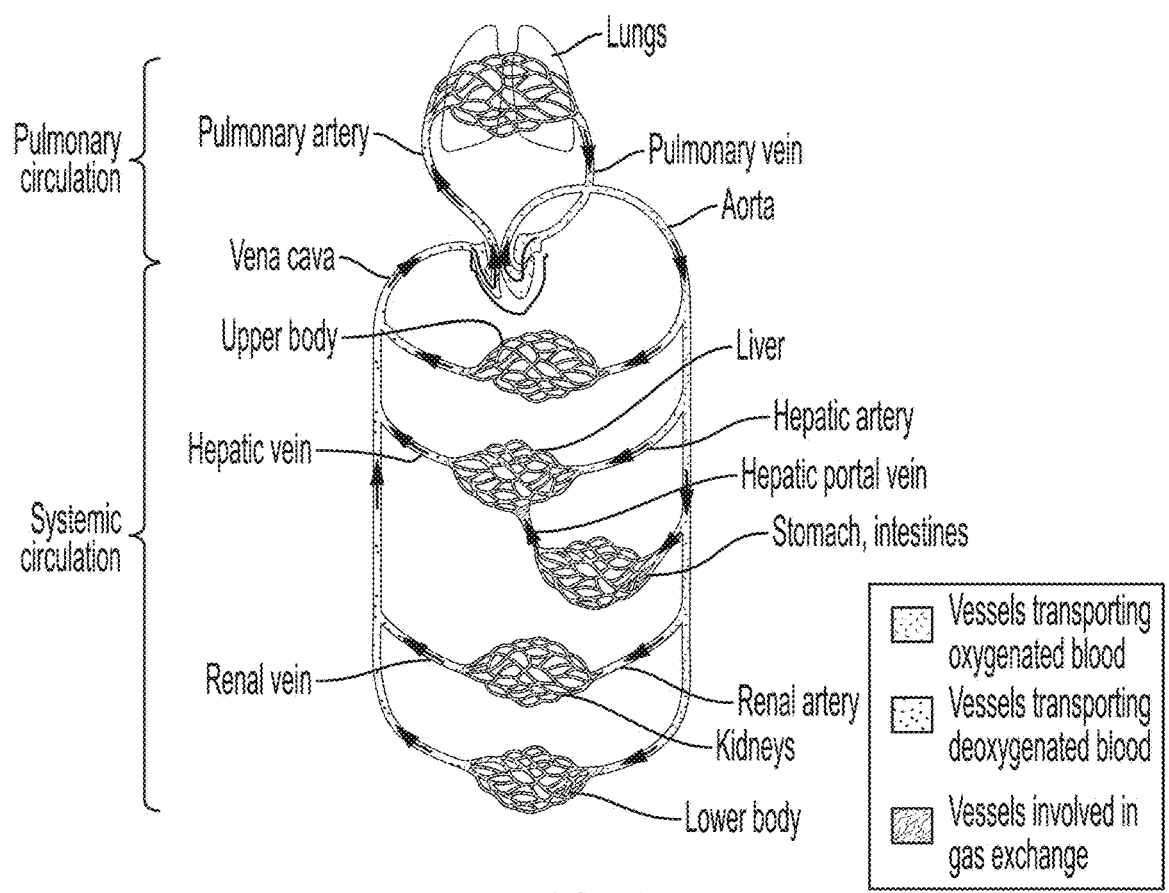
FIG. 9 depicts how certain blood vessels source and sink blood to critical organ circuits that correlate with common cancers.

Certain blood vessels source and sink blood to critical organ circuits that correlate with common cancers, as depicted in FIG. 9. In this FIG. 1 embodiment, blood vessels are used as conductive fluid paths to deliver TTFields to target cancer tumors. For example, TTFields could be delivered to the kidneys by positioning one of the electrodes 10 in the renal vein and another one of the electrodes 10 in the renal artery. Similarly, TTFields could be delivered to the liver by positioning one of the electrodes 10 in the hepatic vein and another one of the electrodes 10 in the hepatic artery.

In some embodiments, the electrodes are inserted directly into the relevant position using a needle shaped electrode that passes through the skin. In other embodiments, the electrodes are guided to their target destinations using one catheter that provides arterial access to the blood inlet of the relevant organ and another catheter that provides venous access to the blood outlet of the relevant organ. For example, to access the liver, one electrode should be inserted in the hepatic artery and another electrode should be inserted in the hepatic vein. Catheter-based access to the hepatic artery and hepatic vein may be obtained by catheters that enter the body via openings e.g., in the femoral artery and femoral vein, respectively. After the electrodes at the distal end of each catheter have arrived at their desired position, an AC voltage is applied between the electrodes while the catheters remain in position.

Alternatively, the electrodes may be implanted into the inlet artery and the outlet vein using the catheters, after which the catheters that were used to deliver the electrodes are removed, leaving only a thin wire behind to provide an electrical connection to the electrodes. When electrodes are implanted into the inlet artery and outlet vein in this manner, the electrodes may be constructed and shaped like conventional arterial stents. In alternative embodiments, the electrodes may be constructed using a mesh or lattice configuration.

In some embodiments, the outer surface of the electrodes 10 is conductive. A suitable material for the outer surface of the electrodes 10 is pyrolytic carbon, which is highly conductive, biocompatible, and known not to form clots/thrombus. This material is therefore suitable for insertion into a person's blood vessels. In alternative embodiments, graphene and activated carbon may be used, both of which have a very high surface area. In alternative embodiments, a biocompatible metal (e.g., gold, titanium, or stainless steel) may be used for the outer surface of the electrodes 10.

In these conductive outer-surface embodiments, a first option is to have the conductive outer surface of each of the electrodes 10 connected via an electrically conductive path to a corresponding terminal of the AC voltage generator 80, with no capacitors interposed between the conductive outer surface of the electrodes 10 and the corresponding terminal of the AC voltage generator 80.

A second option for the conductive outer-surface embodiments is for one or both of the electrodes 10 to have (a) a conductive inner core, (b) a dielectric layer disposed on the conductive inner core, and (c) the conductive outer surface of the electrode disposed on the dielectric layer. When this second option is used, the conductive inner core of each of the electrodes 10 is connected via an electrically conductive path to a corresponding terminal of the AC voltage generator 80. The dielectric layer will act as a capacitor, which means that the AC electric field will be capacitively coupled into the person's body.

Figure 2:
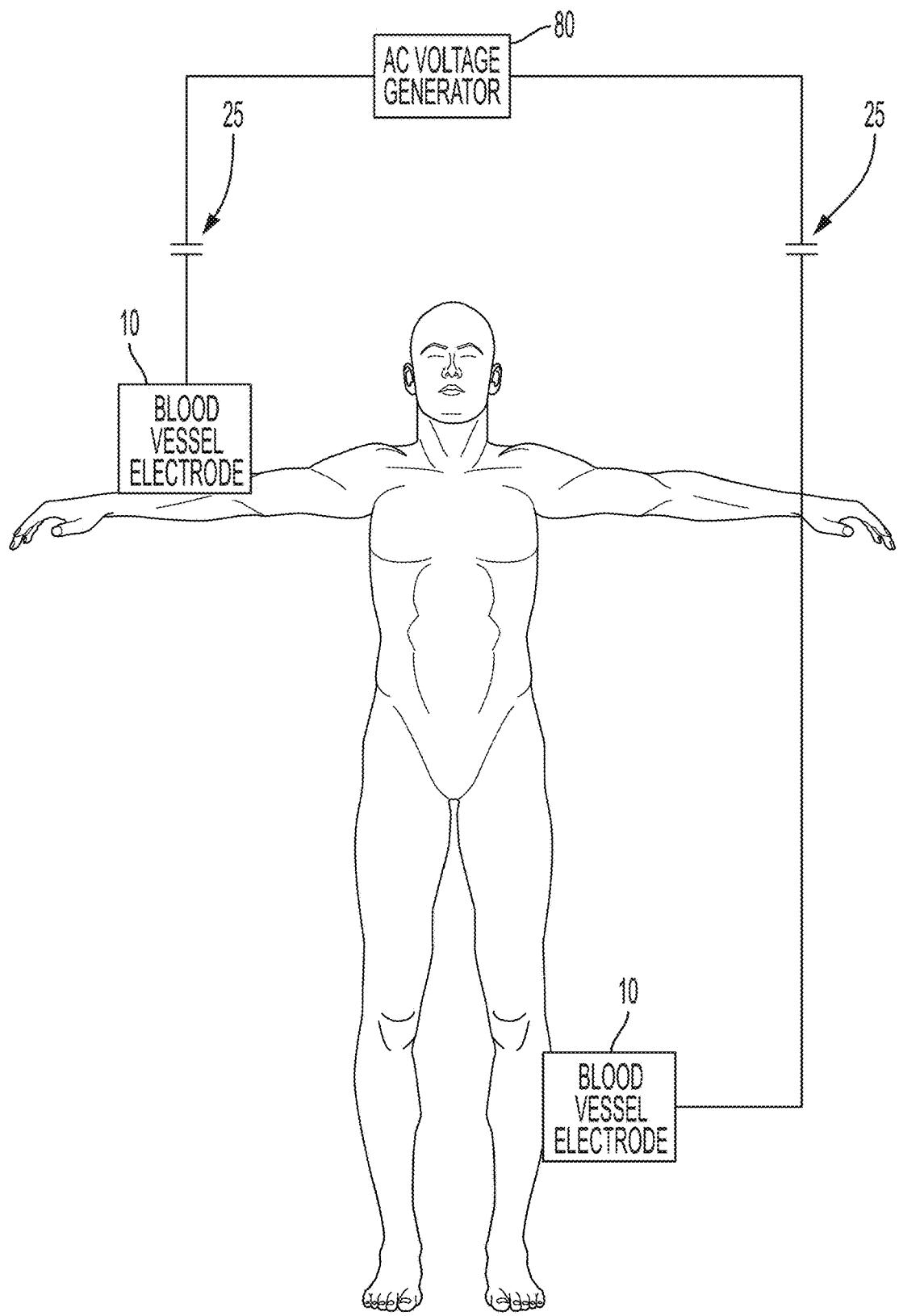
FIG. 2 is a schematic representation of a system for delivering TTFields using electrodes that are shaped and dimensioned for insertion into blood vessels, with added series capacitors.

FIG. 2 depicts yet another option for the conductive outer-surface embodiments. With this third option, the conductive outer surface of each of the electrodes 10 is connected via an electrically conductive path to one terminal of a capacitor 25, and the other terminal of the capacitor 25 is connected via an electrically conductive path to a corresponding terminal of the AC voltage generator 80. Thus, this third option replaces the inherent capacitor that is built into the electrode itself in the second option described above with an external capacitor 25.

The embodiments described above in connection with FIGS. 1 and 2 create an electric field within a volume of a person's blood, and may be used to treat or combat metastases that may be circulating in a person's blood. In addition, particularly when the two electrodes are positioned on either side of a target organ (e.g., kidney, liver, etc.) an electric field will be imposed in the target organ. And notably, because the electrodes can be positioned (a) closer to the target organ and (b) closer to each other (as compared to the conventional approach for positioning the electrodes on the subject's skin on either side of the target organ), it may become easier to impose an electric field in the target organ that is sufficiently high to obtain effective treatment using TTFields.

An additional benefit of positioning the electrodes so that they make contact with blood or CSF is that the conductivity of those two fluids is dramatically higher than the conductivity of skin. Thus, when compared to conventional systems that deliver TTFields via electrodes that are positioned on the skin, a significantly lower voltage will be needed to deliver the same current.

Figure 3A:
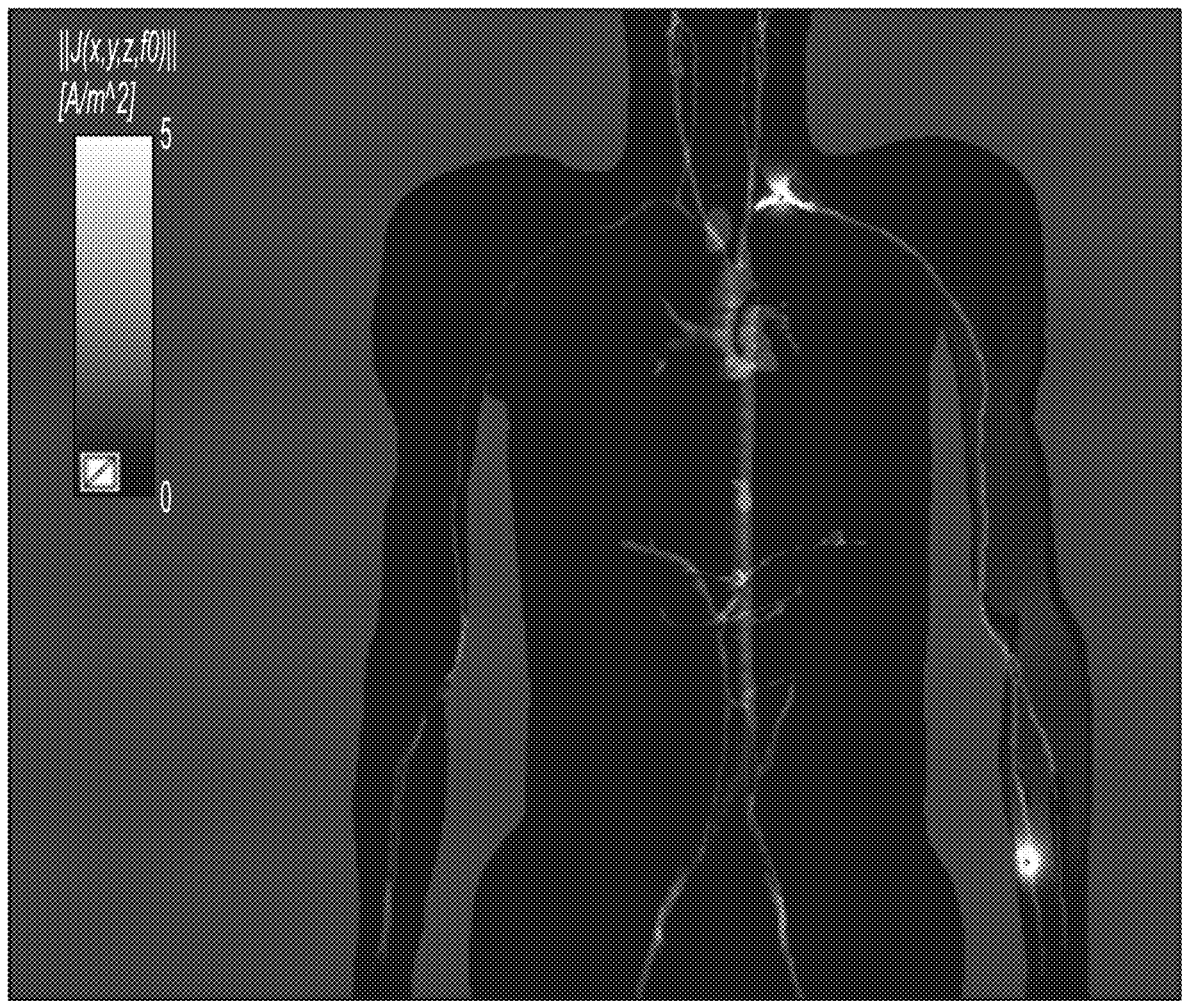
FIGS. 3A-3E depict the results of simulations of the electric field when the electrodes are positioned in various blood vessels in a person's body.
Figure 3B:
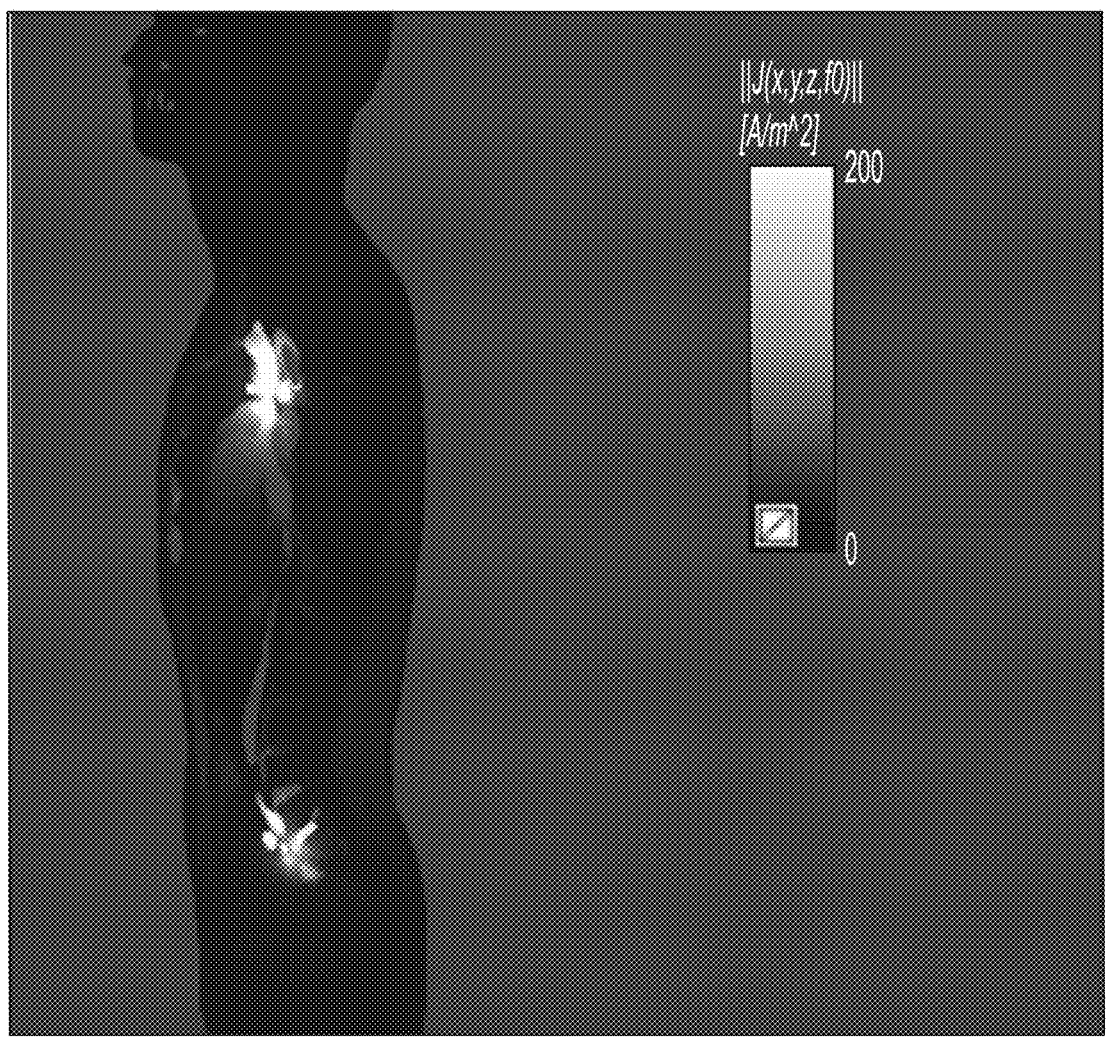
Figure 3C:
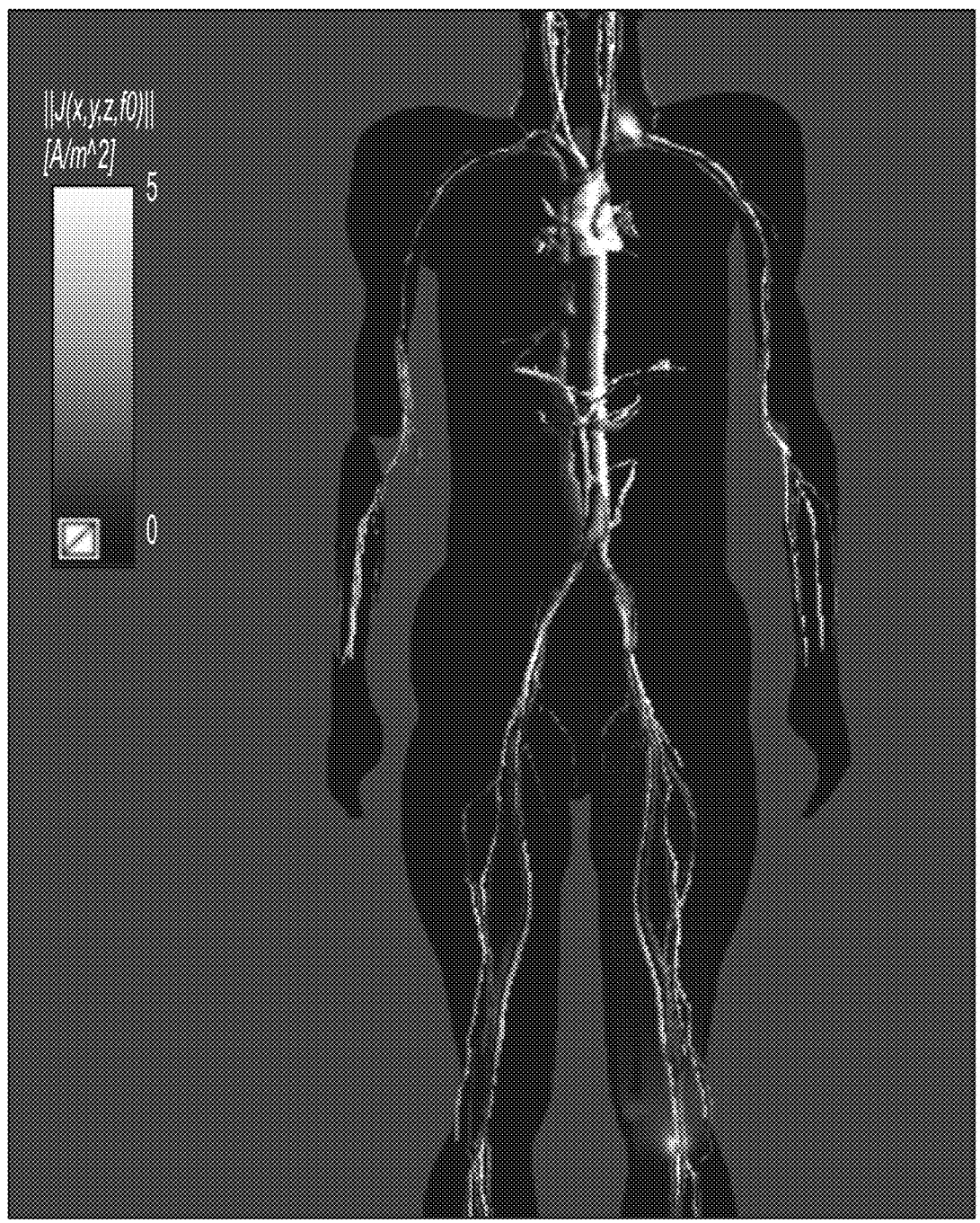
Figure 3D:
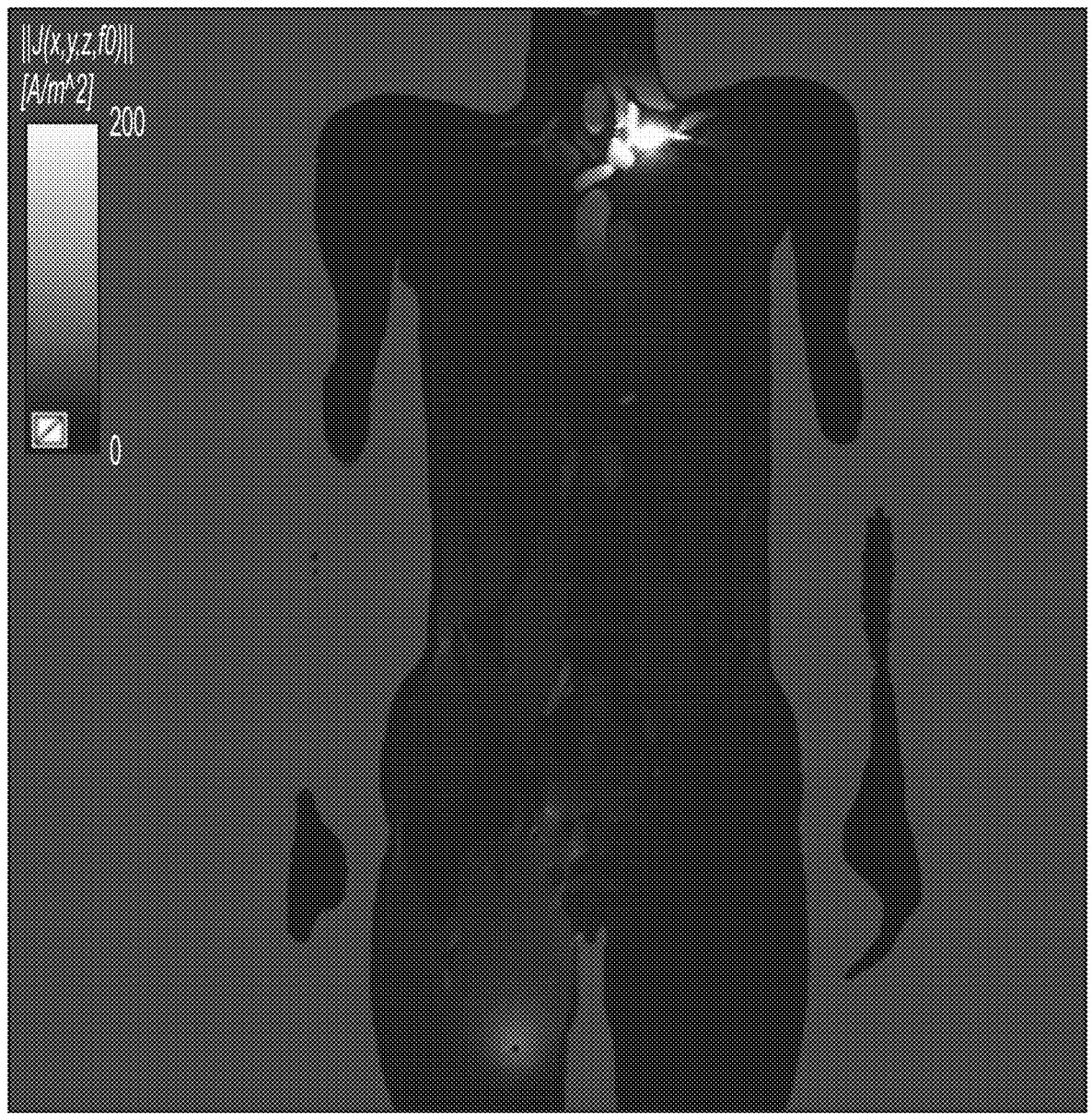
Figure 3E:
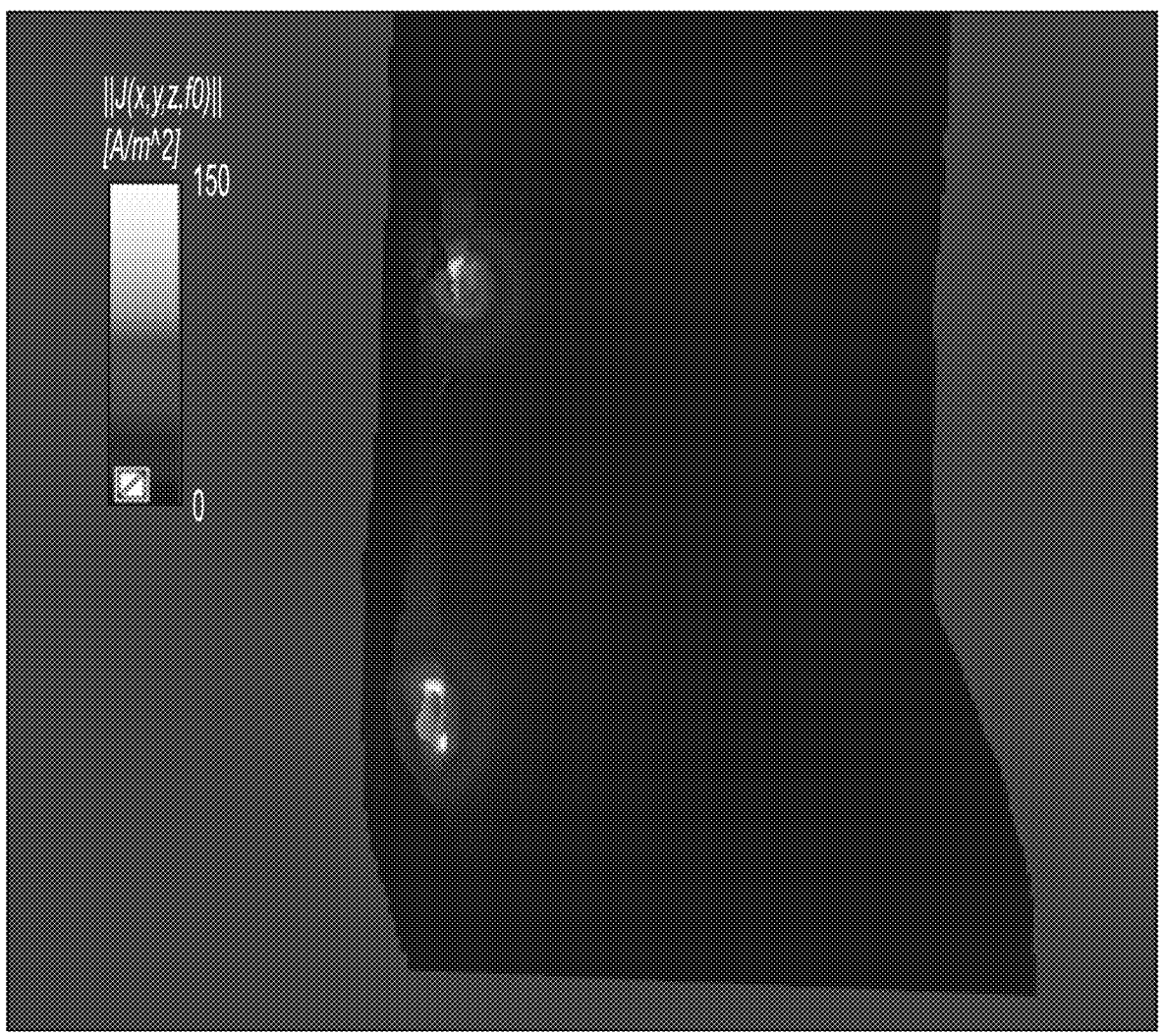

FIGS. 3A-3E depict the results of simulations of the electric field when the electrodes 10 are positioned in various blood vessels in a person's body. In each of these simulations, the strength of the electric field (in A/m 2) is shown in grayscale, with lighter colors corresponding to stronger fields. More specifically, FIG. 3A shows the simulation results when one of the electrodes 10 is positioned in a radial artery and the other electrode 10 is positioned in a shoulder artery; FIG. 3B shows the simulation results when one of the electrodes 10 is positioned in the superior vena cava and the other electrode 10 is positioned in a right iliac vein; FIG. 3C shows the simulation results when one of the electrodes 10 is positioned in a femoral artery and the other electrode 10 is positioned in a shoulder artery; FIG. 3D shows the simulation results when one of the electrodes 10 is positioned in a right thigh vein and the other electrode 10 is positioned in a left shoulder vein; and FIG. 3E shows the simulation results when the electrodes 10 are both positioned in a radial artery, spaced apart by 5 cm.

Figure 4:
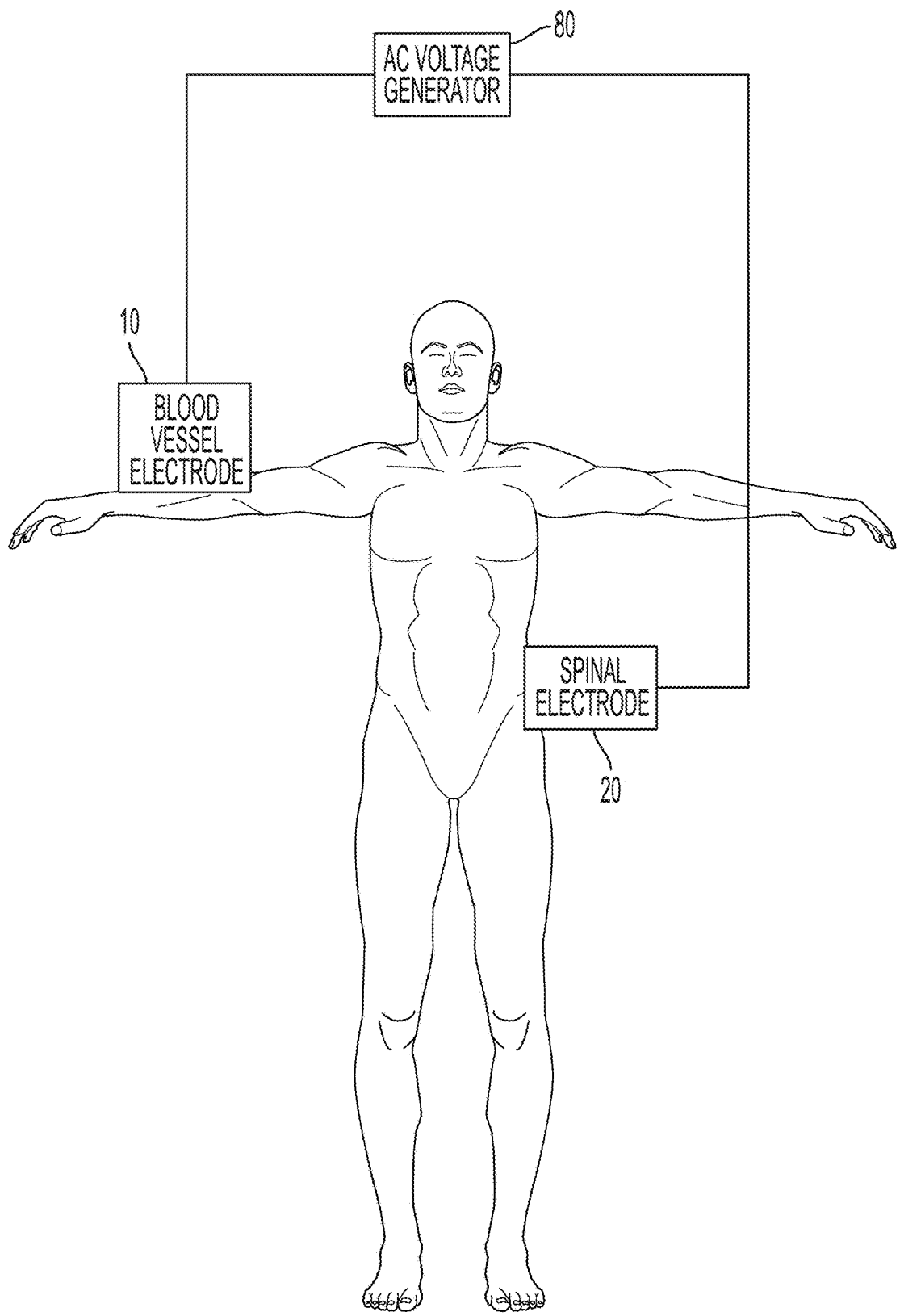
FIG. 4 is a schematic representation of a system for delivering TTFields using electrodes that are shaped and dimensioned for insertion, respectively, into blood vessels and the central canal of a spinal cord.

FIG. 4 depicts one instance of the same electrode 10 (described above in connection with FIGS. 1 and 2), and also includes another electrode 20. This electrode 20 is a second alternative to the conventional external transducer arrays for applying TTFields to portions of a person's body. This electrode 20 is shaped and dimensioned for insertion into a central canal of a spinal cord of the person's body, so that it makes contact with the cerebrospinal fluid (CSF). The outer surface of the electrode 20 is biocompatible. In some embodiments, the electrode 20 has a needle-shaped tip, preferably with a blunt end.

When one electrode 10 is positioned in a blood vessel in a person's body so that it contacts the person's blood, another electrode 20 is positioned in the central canal of the spinal cord so that it contacts the person's CSF, and those two electrodes 10, 20 are connected to the AC voltage generator 80, the AC voltage generator will impose an AC voltage between the two electrodes 10, 20. Because both blood and CSF are highly conductive substances, an electric field will be imposed in the person's body with field lines that run between the two electrodes 10, 20.

In some embodiments, the outer surface of the electrode 20 is conductive. A suitable material for the outer surface of the electro 20 is pyrolytic carbon. Similar to the electrode 10 that is configured for insertion in a blood vessel, a first option for the conductive outer-surface embodiments of the electrode 20 is to have the conductive outer surface of the electrode 20 connected via an electrically conductive path to a corresponding terminal of the AC voltage generator 80, with no capacitors interposed between the conductive outer surface of the electrodes 20 and the corresponding terminal of the AC voltage generator 80.

A second option for the conductive outer-surface embodiments is for the electrode 20 to have (a) a conductive inner core, (b) a dielectric layer disposed on the conductive inner core, and (c) the conductive outer surface of the electrode disposed on the dielectric layer. When this second option is used, the conductive inner core of the electrode 20 is connected via an electrically conductive path to one of the terminals of the AC voltage generator 80. The dielectric layer will act as a capacitor, which means that the AC electric field will be capacitively coupled into the person's body.

Yet another option for the conductive outer-surface embodiments of the electrode 20 is to connect the conductive outer surface of the electrode 20 via an electrically conductive path to one terminal of a capacitor (not shown), and to connect the other terminal of that capacitor via an electrically conductive path to a corresponding terminal of the AC voltage generator 80. (This is similar to the configuration depicted in FIG. 2 for the blood vessel electrodes 10.)

Figure 5:
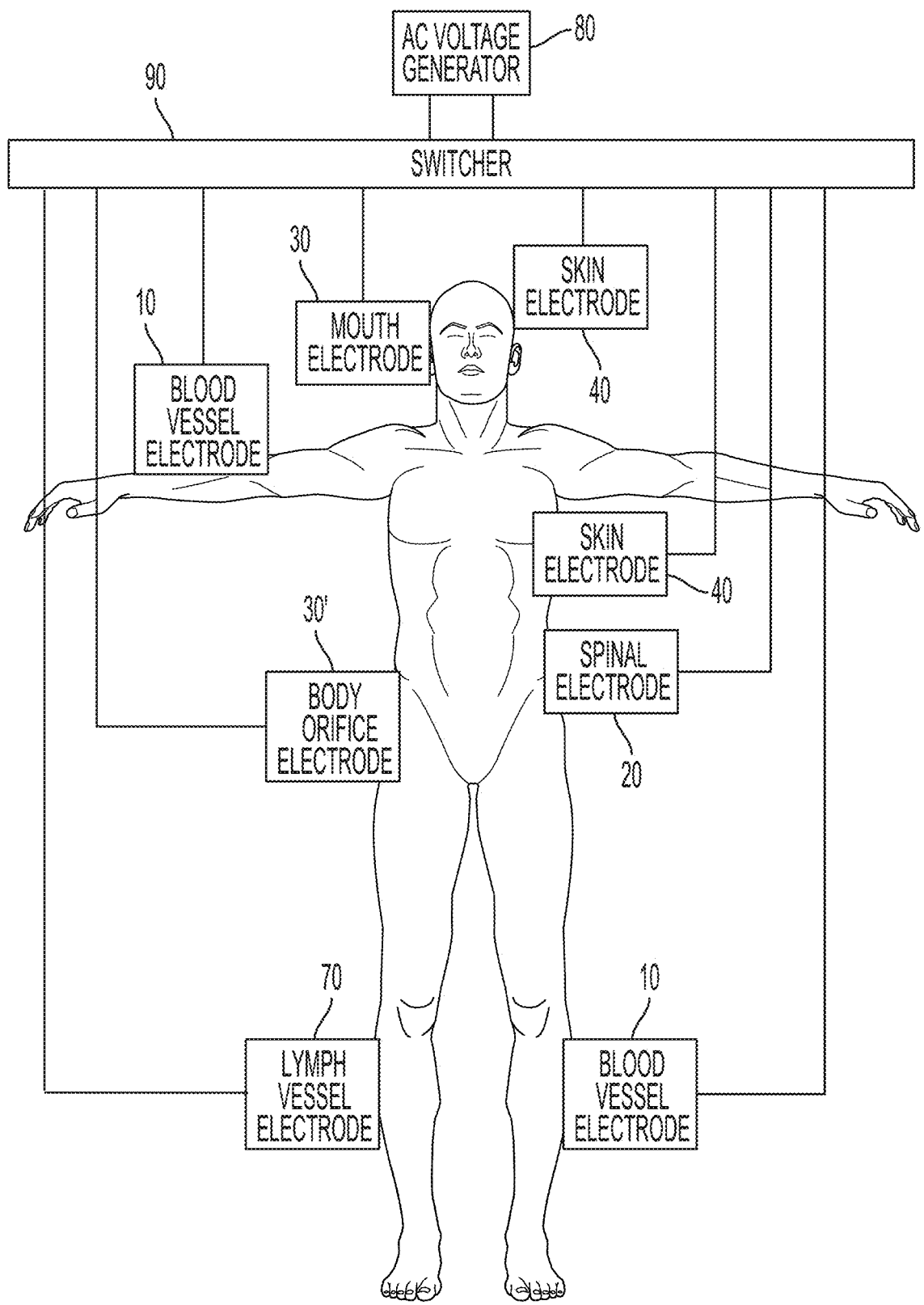
FIG. 5 is a schematic representation of a system for delivering TTFields using four alternatives to the conventional external transducer arrays for applying TTFields.

FIG. 5 depicts three alternatives 10, 20, 30/30' to the conventional external transducer arrays for applying TTFields, and also depicts two conventional external transducer arrays 40 for applying TTFields to portions of a person's body. The first alternative is the electrode 10 that is shaped and dimensioned for insertion into a blood vessel of the person's body so that it makes contact with the person's blood; and this alternative is described above in connection with FIGS. 1 and 2. The second alternative is the electrode 20 that is shaped and dimensioned for insertion into a central canal of a spinal cord of the person's body, so that it makes contact with the CSF; and this alternative is described above in connection with FIG. 4.

The third alternative is an electrode 30 or 30' that is shaped and dimensioned for insertion into a body orifice of the person at a position that contacts an interior surface of the person's body. Examples of suitable orifices that can accept the electrode 30/30' include the rectum, the vagina, urethra, and the mouth. Shaping and dimensioning of these electrodes 30/30' will depend on the particular body orifice into which the electrode 30/30' is inserted. For example, in the case of the rectum or vagina, a suitable shape would be a cylindrical body with a rounded tip, a diameter of 0.5-1 inch, and a length of 1-3 inches. In another example, a suitable shape for insertion into a person's mouth would be similar to that of a palatal expander, with an upper surface customized to contact the roof of the mouth of the particular person that will be treated.

Figure 6A:
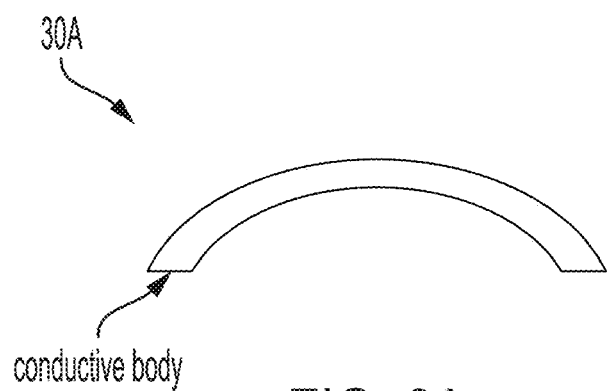
FIGS. 6A-6C depict three options for constructing the body orifice electrodes depicted in FIG. 5.
Figure 6B:
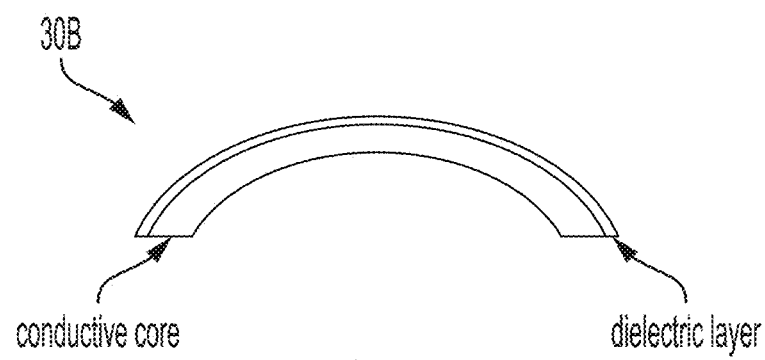
Figure 6C:
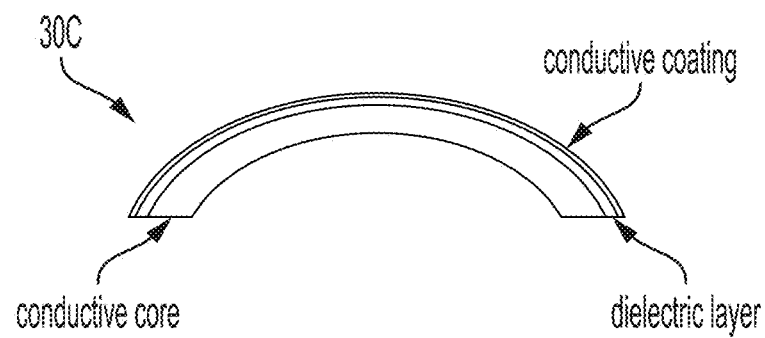

Three options for constructing the body orifice electrodes 30 are depicted in FIGS. 6A-6C. More specifically, FIGS. 6A-6C depict three examples of electrodes 30A, 30B, 30C, each of which is configured for positioning in contact with the roof of the person's mouth, all shown in cross-section. In the FIG. 6A option, the electrode 30A has a conductive body that is shaped and dimensioned for insertion into a body orifice (e.g., the mouth) of the person at a position that contacts an interior surface (e.g., the pallet) of the person's body. The conductive body in this option is connected via an electrically conductive path to a corresponding terminal of the AC voltage generator 80, with no capacitors interposed between the conductive body and the corresponding terminal of the AC voltage generator 80.

In the FIG. 6B option, the electrode 30B has a conductive core that is shaped and dimensioned for insertion into a body orifice (e.g., the mouth) of the person at a position that contacts an interior surface (e.g., the pallet) of the person's body. A dielectric layer is disposed on the conductive core so that it sits between the conductive core and the internal surface of the body. With this option, the conductive core is connected via an electrically conductive path to a corresponding terminal of the AC voltage generator 80. The dielectric layer will act as a capacitor, which means that the AC electric field will be capacitively coupled into the person's body.

In the FIG. 6C option, the electrode 30C has a conductive core that is shaped and dimensioned for insertion into a body orifice (e.g., the mouth) of the person at a position that contacts an interior surface (e.g., the pallet) of the person's body. A dielectric layer is disposed on the conductive core so that it sits on the outer side of the conductive core, and an additional conductive coating is disposed on the dielectric layer so that it sits between the dielectric layer and the internal surface of the body. Examples of suitable materials for this conductive coating include stainless steel and pyrolytic carbon. With this option, the conductive core is connected via an electrically conductive path to a corresponding terminal of the AC voltage generator 80. The dielectric layer in this option also acts as a capacitor.

Returning now to FIG. 5, the fourth alternative is an electrode 40 that is shaped and dimensioned for affixation to skin of the person's body (e.g., on the person's head, torso, back, abdomen, etc.). This alternative may be implemented using, for example, the conventional transducer arrays from the Optune® system, available from Novocure™ And a fifth alternative is an electrode 70 that is shaped and dimensioned for insertion into a lymph vessel of the person's body so that it makes contact with the person's lymph. This alternative is similar to the blood vessel electrode described above, appropriately scaled for size.

An electric field may be created within the person's body by applying an AC voltage between any two of the electrodes 10, 20, 30, 30', 40, 70 depicted in FIG. 5. In one example, an electric field may be created by applying an AC voltage between the two electrodes 10 (i.e., two electrodes each of which is shaped and dimensioned for insertion into a blood vessel). In another example, an electric field may be created by applying an AC voltage between an electrode 10 (i.e., an electrode shaped and dimensioned for insertion into a blood vessel) and an electrode 20 (i.e., an electrode shaped and dimensioned for insertion into a central canal of a spinal cord). In another example, an electric field may be created by applying an AC voltage between an electrode 10 (i.e., an electrode shaped and dimensioned for insertion into a blood vessel) and an electrode 30 (i.e., an electrode shaped and dimensioned for insertion into a body orifice at a position that contacts the interior surface of the person's body). In another example, an electric field may be created by applying an AC voltage between an electrode 10 (i.e., an electrode shaped and dimensioned for insertion into a blood vessel) and an electrode 40 (i.e., an electrode shaped and dimensioned for affixation to skin). In another example, an electric field may be created by applying an AC voltage between an electrode 10 (i.e., an electrode shaped and dimensioned for insertion into a blood vessel) and an electrode 70 (i.e., an electrode shaped and dimensioned for insertion into a lymph vessel).

In another example, an electric field may be created by applying an AC voltage between an electrode 20 (i.e., an electrode shaped and dimensioned for insertion into a central canal of a spinal cord) and an electrode 30 (i.e., an electrode shaped and dimensioned for insertion into a body orifice at a position that contacts the interior surface of the person's body). In another example, an electric field may be created by applying an AC voltage between an electrode 20 (i.e., an electrode shaped and dimensioned for insertion into a central canal of a spinal cord) and an electrode 40 (i.e., an electrode shaped and dimensioned for affixation to skin).

In another example, an electric field may be created by applying an AC voltage between two electrodes 30, each of which is shaped and dimensioned for insertion into a body orifice at a position that contacts the interior surface of the person's body. In yet another example, an electric field may be created by applying an AC voltage between an electrode 30 (i.e., an electrode shaped and dimensioned for insertion into a body orifice at a position that contacts the interior surface of the person's body) and an electrode 40 (i.e., an electrode shaped and dimensioned for affixation to skin).

The switcher 90 switches the output of the AC voltage generator 80 to any two of the electrodes 10, 20, 30, 30', 40, 70 to create any of the electric fields described above in connection with this figure (i.e., FIG. 5). Optionally, the output of the AC voltage generator 80 may be switched between different pairs of those electrodes sequentially. For example, the switcher 90 could (a) route the output of the AC voltage generator 80 between the head electrode 40 and the mouth electrode 30 for a first period of time (e.g., one second), then (b) route the output of the AC voltage generator 80 between the mouth electrode 30 and the arm electrode 10 for a second period of time (e.g., one second), then repeat that two-step sequence (a), (b) for the duration of the treatment.

Figure 7:
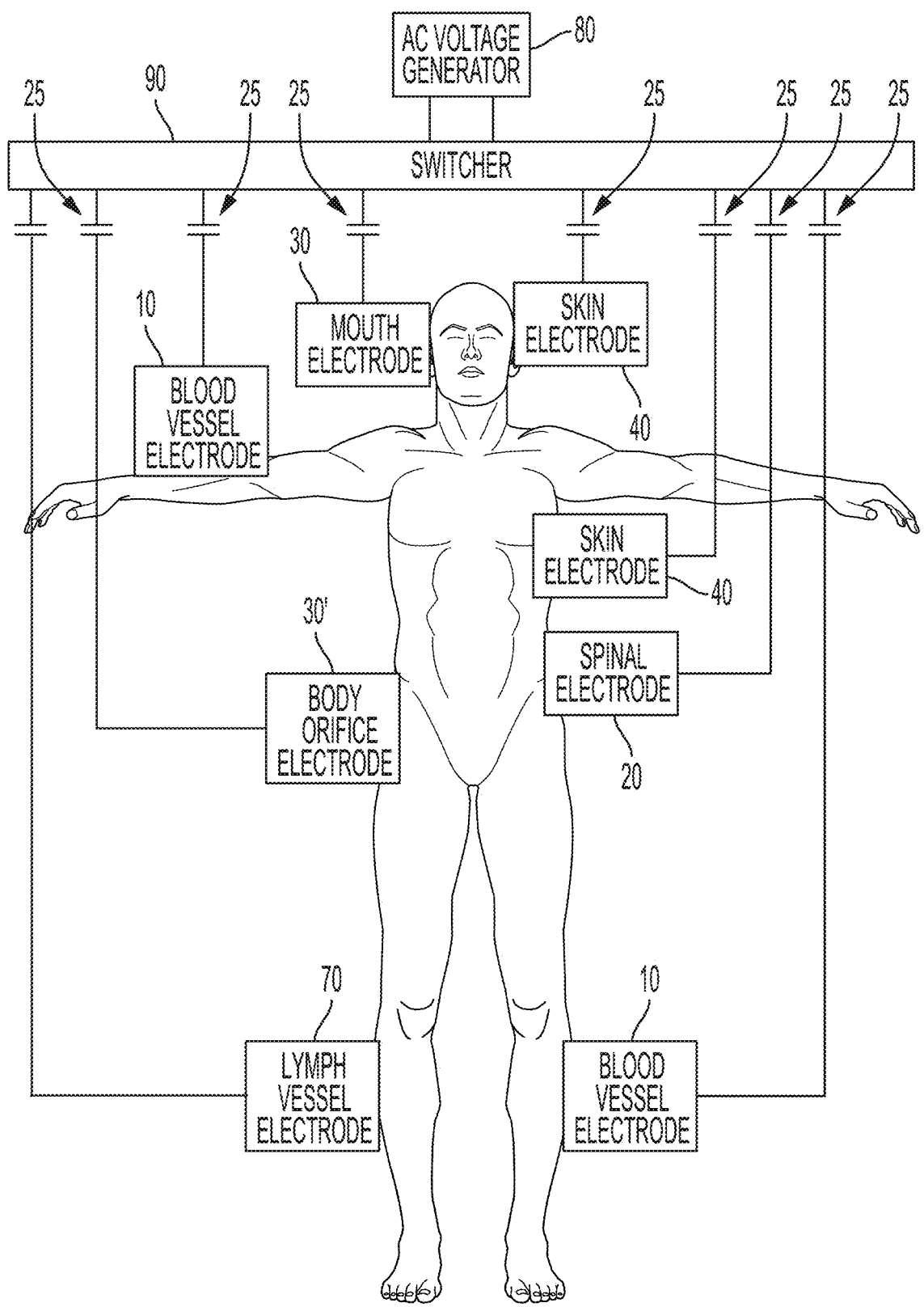
FIG. 7 is a schematic representation of a system for delivering TTFields using that is similar to the FIG. 5 embodiment, with added series capacitors.

FIG. 7 depicts a configuration that is similar to the FIG. 5 embodiment discussed above, but adds one or more capacitors 25 in series with respective electrodes 10, 20, 30, 30', 40, 70. This configuration is preferably used when the electrodes themselves are completely conductive, and do not incorporate a dielectric layer. In the FIG. 7 embodiments, the conductive outer surface of each of the electrodes 10 is connected via an electrically conductive path to one terminal of a capacitor 25, and the other terminal of the capacitor 25 is connected via an electrically conductive path to a corresponding terminal of the AC voltage generator 80 via the switcher 90.

Figure 8:
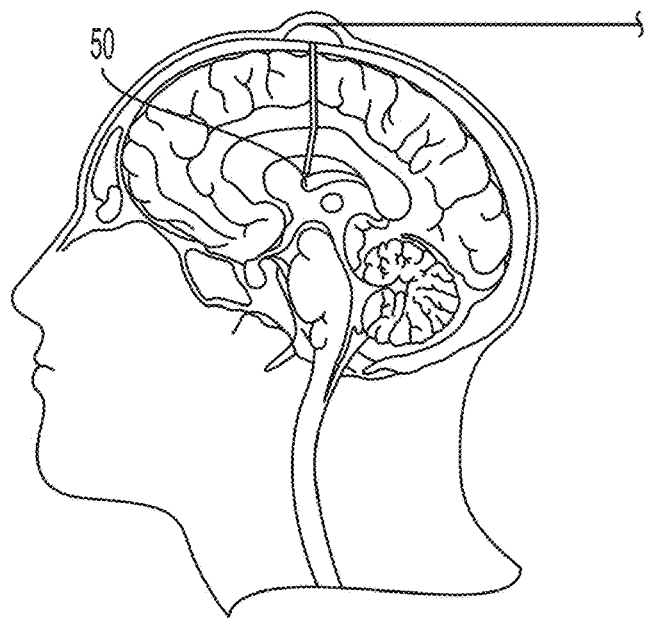
FIG. 8 depicts an electrode for delivering TTFields that is shaped and dimensioned for insertion into a brain ventricle.

FIG. 8 depicts yet another alternative to the conventional external transducer arrays for applying TTFields to portions of a person's body. This alternative relies on an electrode 50 for delivering TTFields that is shaped and dimensioned for insertion into a brain ventricle of the person's body, so that it makes contact with the CSF in the ventricle. The outer surface of the electrode 50 is biocompatible. In some embodiments, the electrode 50 has a shape that is similar to the Ommaya intraventricular catheter system, which is used to access a brain ventricle.

The brain ventricle electrode 50 in this FIG. 8 embodiment is combined with one or more of the other varieties of electrodes 10/20/30/40/70 described above. When one electrode 50 is positioned in a brain ventricle in a person's body so that it contacts the CSF, and a second electrode 10/20/30/40/70 is positioned in either a blood vessel, the spinal cord, a body orifice, on a body surface, or in a lymph vessel, and those two electrodes 50, 10/20/30/40/70 are connected to the AC voltage generator 80, the AC voltage generator will impose an AC voltage between the two electrodes 50, 10/20/30/40.

In some embodiments, the outer surface of the electrode 50 is conductive. A suitable material for the outer surface of the electro 50 is pyrolytic carbon. Similar to the electrode 10 that is configured for insertion in a blood vessel, a first option for the conductive outer-surface embodiments of the electrode 50 is to have the conductive outer surface of the electrode 50 connected via an electrically conductive path to a corresponding terminal of the AC voltage generator 80, with no capacitors interposed between the conductive outer surface of the electrodes 50 and the corresponding terminal of the AC voltage generator 80.

A second option for the conductive outer-surface embodiments is for the electrode 50 to have (a) a conductive inner core, (b) a dielectric layer disposed on the conductive inner core, and (c) the conductive outer surface of the electrode disposed on the dielectric layer. When this second option is used, the conductive inner core of the electrode 50 is connected via an electrically conductive path to one of the terminals of the AC voltage generator 80. The dielectric layer will act as a capacitor, which means that the AC electric field will be capacitively coupled into the person's body.

Yet another option for the conductive outer-surface embodiments of the electrode 50 is to connect the conductive outer surface of the electrode 50 via an electrically conductive path to one terminal of a capacitor (not shown), and to connect the other terminal of that capacitor via an electrically conductive path to a corresponding terminal of the AC voltage generator 80. (This is similar to the configuration depicted in FIG. 2 for the blood vessel electrodes 10.)

Notably, CSF has a very high conductivity and is positioned in the immediate vicinity of many types of brain tumors. Positioning an electrode in contact with the CSF and applying a voltage to the electrode can therefore be a very convenient access point for inducing an electric field in those brain tumors.

Figure 10:
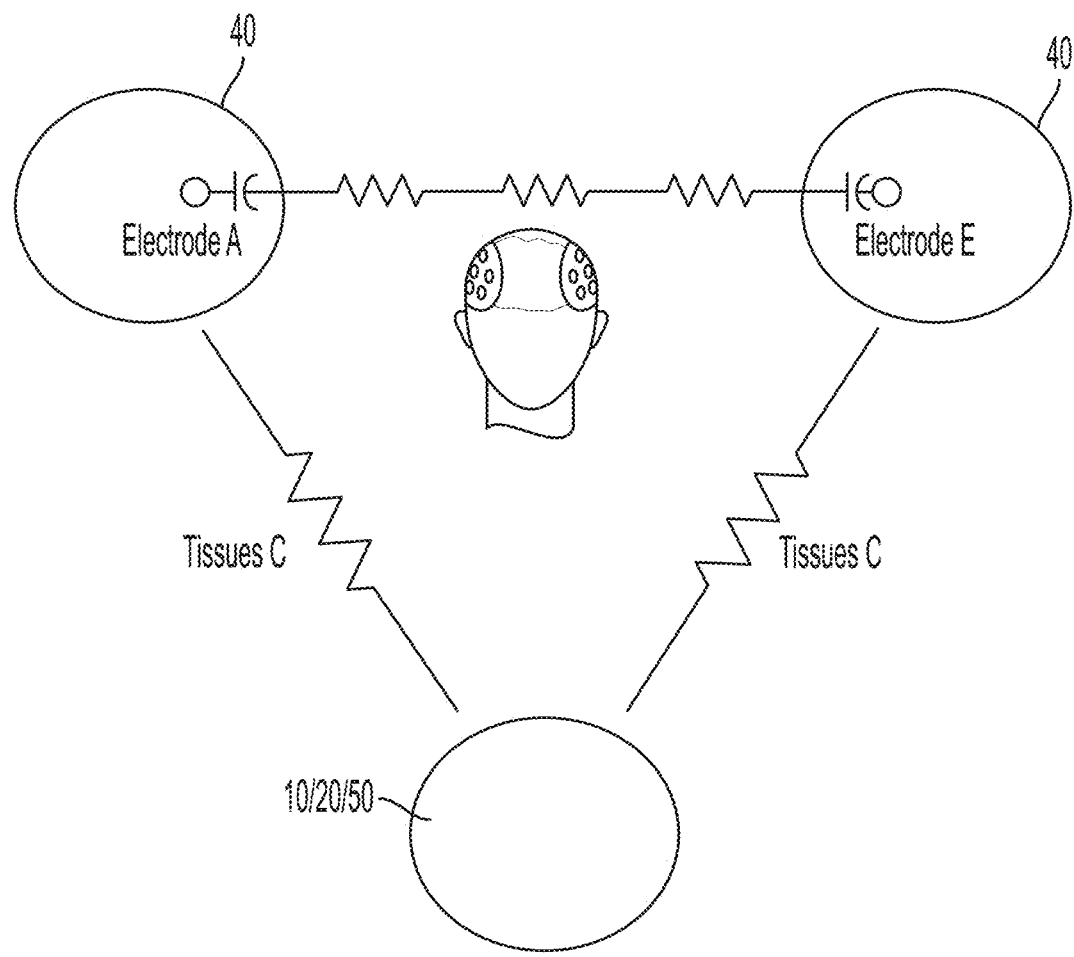
FIG. 10 schematically depicts the resistance that is encountered when one electrode is positioned in contact with either blood or CSF, and the remaining electrodes are positioned on the person's skin.

FIG. 10 schematically depicts the resistance that is encountered when one of the electrodes is positioned in contact with either blood, CSF, or lymph, and the remaining electrodes are conventional electrodes 40 positioned on the person's skin. More specifically, the blood vessel electrodes 10, the spinal electrodes 20, the ventricular electrodes 50, and the lymph vessel electrodes 70 described above establish a high conductivity/low resistance path into a person's body, because those electrodes are positioned in contact with a high conductivity fluid (i.e., blood, CSF, or lymph). When a single one of those electrodes 10/20/50/70 combined in a system with one or more conventional electrodes 40 that are positioned on a person's skin, the electrode 10/20/50/70 will establish an electrical path to the tissues with relatively low resistance. On the other hand, the conventional electrodes 40 will establish an electrical path to the tissue with a higher resistance due to the relatively high resistance of skin. Note that while two conventional electrodes 40 are depicted in FIG. 10, a different number (e.g., 1-6) of conventional electrodes 40 may be used.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating a portion of a person's body with an electric field, the method comprising:
   inserting a first electrode into a central canal of a spinal cord of the person's body, the first electrode having a biocompatible outer surface;
   positioning a second electrode on or in the person's body, wherein the second electrode is either (a) inserted into a blood vessel of the person's body, (b) inserted into the central canal of the spinal cord of the person's body, (c) inserted into a body orifice of the person at a position that contacts an interior surface of the person's body, (d) affixed to skin of the person's body, or (e) inserted into a lymph vessel of the person's body; and
   applying an AC voltage between the first electrode and the second electrode.

2. The method of claim 1, wherein the outer surface of the first electrode is conductive.

3. The method of claim 1, wherein the outer surface of the first electrode comprises pyrolytic carbon.

4. The method of claim 1, wherein the positioning of the second electrode comprises inserting the second electrode into the central canal of the spinal cord of the person's body.

5. The method of claim 1, further comprising positioning a capacitor in series with the first electrode.

6. The method of claim 1, further comprising positioning a capacitor in series with the second electrode.

* * * * *